United States Patent
Widmer

(10) Patent No.: US 6,904,815 B2
(45) Date of Patent: Jun. 14, 2005

(54) CONFIGURABLE MULTI-POINT SAMPLING METHOD AND SYSTEM FOR REPRESENTATIVE GAS COMPOSITION MEASUREMENTS IN A STRATIFIED GAS FLOW STREAM

(75) Inventor: Neil Colin Widmer, Irvine, CA (US)

(73) Assignee: General Electric Company, Schenectady, NY (US)

(*) Notice: Subject to any disclaimer, the term of this patent is extended or adjusted under 35 U.S.C. 154(b) by 48 days.

(21) Appl. No.: 10/605,794

(22) Filed: Oct. 28, 2003

(65) Prior Publication Data

US 2005/0087027 A1  Apr. 28, 2005

(51) Int. Cl.[7] .............................. G01N 1/16; G01N 1/26
(52) U.S. Cl. .................................... 73/863.03; 73/863.31
(58) Field of Search ........................ 73/863.02, 863.03, 73/863.31, 863.32, 863.33, 863.81, 864.81

(56) References Cited

U.S. PATENT DOCUMENTS

| | | | |
|---|---|---|---|
| 3,842,678 A | * 10/1974 | De Baun et al. ......... 73/863.03 |
| 3,930,414 A | 1/1976 | Russell |
| 4,150,574 A | 4/1979 | Wolf |
| 4,413,533 A | * 11/1983 | Diesel .................... 73/863.31 |
| 4,442,720 A | * 4/1984 | Apley et al. ............ 73/863.31 |
| 4,566,342 A | * 1/1986 | Kurz ....................... 73/863.03 |
| 4,660,587 A | * 4/1987 | Rizzie ........................... 137/8 |
| 4,860,598 A | 8/1989 | Bailey et al. |
| 6,241,950 B1 | * 6/2001 | Veelenturf et al. .......... 422/103 |
| 2003/0019304 A1 | * 1/2003 | Taylor et al. ........... 73/863.03 |

* cited by examiner

Primary Examiner—Charles Garber
(74) Attorney, Agent, or Firm—Nixon & Vanderhye P.C.

(57) ABSTRACT

A method and system of obtaining a sample of fluid flowing through a duct comprises determining an average concentration of a component species of the fluid during a test including determining first and second concentrations of the component species at first and second respective duct locations, positioning first and second sample probes in the duct so that they receive the fluid at the first and second locations, respectively, and controlling respective flow rates of fluid received by the first and second sample probes, or alternatively first and second time amounts that the flow of fluid is received by the first and second sample probes, respectively, based on the determined first, second and average concentrations. The respective flow rates or time amounts may be controlled so that component species concentration collectively received by the first and second sample probes equals the average concentration of the component species determined during the test.

63 Claims, 2 Drawing Sheets

CONFIGURABLE MULTI-POINT SAMPLING METHOD AND SYSTEM FOR REPRESENTATIVE GAS COMPOSITION MEASUREMENTS IN A STRATIFIED GAS FLOW STREAM

CROSS REFERENCE TO RELATED APPLICATIONS

This application is related to commonly assigned U.S. application Ser. No. 10/605,795 entitled "A Multi-point Sampling Method for Obtaining Isokinetic Fluid Composition Flows in a Non-Uniform Velocity Flow Field", filed concurrently herewith and naming Neil C. Widmer as inventor, the contents of which are incorporated herein by reference.

BACKGROUND OF INVENTION

The present invention relates to a method and system of obtaining a spatially representative sample of fluid flowing in a duct, and particularly relates to a method and system of obtaining a spatially representative sample of fluid utilizing multiple sampling probes.

Emissions flowing in an exhaust stack of a gas turbine have been routinely sampled for many years. This sampling may indicate when emissions contain certain concentrations of pollutants. It is thus necessary to ensure that the emissions are sampled accurately.

Non-representative gas sampling in exhaust streams is a significant contributor to inaccurate low level gas species (emissions) measurements. For gas turbine applications, many units are being certified at 9 ppm and even as low as 2 to 3 ppm, all normalized to a diluent level of 15% oxygen. In these applications, the effect of a non-representative oxygen sample being off by 0.5% translates to a 7%–15% bias in NOx emissions depending on the excess oxygen exhaust concentration. Additionally, NOx and other pollutant species like CO and NH3 can be highly stratified resulting in large variations of species concentrations.

A current process to achieve representative sampling of an exhaust stream involves measuring multiple points across the stack. This current process is generally a manual process that is not suitable for continuous monitoring systems. Points sampled depend on test method: for 40 CFR 60, App A, Method 20 (turbines) eight points at the lowest O2 levels are sampled, for RATAs (40 CFR 60, App. B) three points are sampled, and for Part 75 between one and three points are sampled.

While multipoint sampling is widely used to obtain a representative sample of fluid, it typically involves a manual process of inserting a sample probe to various locations in the fluid stream. This sampling process is thus laborious and time consuming as it requires multiple measurements to determine the gas velocity and then full-time attendance of a sample metering pump to draw flow through a port of known area at specific flow rates.

When manually sampling at the various locations in the stream, the gas is extracted at equal gas volumes per point. This approach ensures a volume averaged gas concentration across the flow. Obtaining volume averaged flow requires point information on the gas volume flow rate and temperature and point specific flow rate control.

Simple solutions to achieve multipoint sampling often involve using a single probe with multiple sampling holes spaced along the probe length. However, because it involves a common sample line, this approach does not allow easy and on-line adjustment of the flow rate sampled at each point.

A variation to this solution employs a sample probe with critical pressure drop at the sample probe inlets. A sample pump draws flow into the multiple probe inlets at equal volumes independent of the probe location. This avoids problems with variation in flow due to pressure drop along the sampling probe, so sampling points further into the flow are equally represented. However, it does not provide an isokinetic flow. For example, when sampling in a low flow and high flow region, both points are equally represented. This sampling biases the true impact of the low flow. If the low flow region contained twice as much pollutant concentrations but only half as much flow as the high flow region, then the overall emissions would be overly biased (i.e., biased high). As a quantitative example of this overly biased sampling, suppose a low flow region constituted 25% of the entire exhaust flow and contained 10 ppm of NOx and a high flow region constituted 75% of the entire exhaust flow and contained 5 ppm of NOx. In this quantitative example, the flow averaged emission is OLE_LINK1(25%)(10 ppm NOx)+(75%)(5 ppm NOx) OLE_LINK1=6.25 ppm NOx. However, the sampling system would determine the result as 7.5 ppm NOx via the following calculation: (50%)(10 ppm NOx)+(50%)(5 ppm NOx)=7.5 ppm NOx.

In sampling systems where critical pressure drop is not established at the port inlet, further bias can be introduced due to sample line length and pressure head differences. In these cases, sampling further into a flow stream would have higher line pressure losses and lower sampling rates. Assuming the above quantitative example, if the high flow region was in the center of a stack (i.e., center of the flow) and the low flow region was closer to the wall of the stack, and the high flow region formed 45% of the total flow and the low flow region formed 55% of the total flow due to sample line pressure differences, the determined results would be further biased at 7.75 ppm NOx as calculated as follows: (55%)(10 ppm NOx)+(45%)(5 ppm NOx)=7.75 ppm NOx.

Other systems utilize a sampling grid having multiple sampling probes spatially distributed across the flow field. In these systems, the flow is typically drawn through a common pump and is sequenced to get point-to-point sample concentrations rather than average sample concentrations.

There thus remains a need for a method and system of obtaining a more spatially representative sample utilizing multiple sampling probes.

SUMMARY OF INVENTION

In a first exemplary aspect of the invention, a method and system of obtaining a spatially representative sample of fluid flowing through a duct comprises (i) determining an average concentration of a component species of the fluid flowing through the duct during a test which includes determining a first concentration of the component species fluid at a first location within the duct and determining a second concentration of the component species at a second location within the duct, (ii) positioning a first sample probe in the duct so that the first sample probe receives a portion of the fluid at the first location; (iii) positioning a second sample probe in the duct so that the second sample probe receives a portion of the fluid at the second location, and (iv) controlling respective flow rates of fluid received by the first and second sample probes based on the first concentration of the component species, the second concentration of the component species and the average concentration of the component species. The respective flow rates may be controlled so that a concentration of the component species of the fluid collectively received by the first and second sample probes equals the average concentration of the component species determined during the test. The first and second concentrations of the component species determined during the test may be different from each other. The fluid may be received by the first and second sample probes concurrently. The flow rate of the fluid received by the first sample probe may be controlled by a first flow controller connected to the first sample probe and the flow rate of the fluid received by the second sample probe may be controlled by a second flow controller connected to the second sample probe. The test may be a stratification test. The component species may be at least one of O2, CO2, CO, SO2 and NOx. Determining the average concentration of the component species during the test may further include determining a third concentration of the component species of the fluid at a third location within the duct, and respective flow rates of fluid received by the first and second sample probes and a third sample probe at the third location are controlled based on the first, second and third concentrations of the component species determined during the test and the average concentration of the component species determined by the test. The respective flow rates of fluid received by the first, second and third sample probes are controlled so that a concentration of the component species collectively received by the first, second and third sample probes may equal the average concentration of the component species determined during the test. The first, second and third concentrations of the component species determined during the test may be different from each other.

In another exemplary aspect of the invention, a method and system of obtaining a spatially representative sample of fluid flowing through a duct comprises: (i) determining an average concentration of a component species of the fluid flowing through the duct during a test which includes determining a first concentration of the component species at a first location within the duct and determining a second concentration of the component species at a second location within the duct, (ii) positioning a first sample probe in the duct so that the first sample probe receives a portion of the fluid at the first location, (iii) positioning a second sample probe in the duct so that the second sample probe receives the fluid at the second location, and (iv) controlling a first amount of time that the flow of fluid is received by the first sample probe and a second amount of time that the flow of fluid is received by the second sample probe based on the first concentration of the component species, the second concentration of the component species and the average concentration of the component species. The first amount of time and the second amount of time may be controlled so that a concentration of the component species of the fluid collectively received by the first and second sample probes equals the average concentration of the component species determined during the test. The first and second concentrations of the component species determined during the test may be different from each other. The fluid may be received by the first and second sample probes non-concurrently. The method and system may further comprise venting fluid from the first sample probe when fluid is being received by the second sample probe and venting fluid from the second sample probe when the fluid is being received by the first sample probe. The first amount of time that the fluid is received by the first sample probe may be controlled by a first flow controller connected to the first sample probe and the second amount of time that the fluid is received by the second sample probe may be controlled by a second flow controller connected to the second sample probe. At least one of the first and second flow controllers is coupled to both a sample pump and a venting pump. The first flow controller may vent fluid from the first sample probe when the second flow controller communicates fluid received by the second flow controller to a sample pump. The second flow controller may vent fluid from the second sample probe when the first flow controller communicates fluid received by the first flow controller to a sample pump. The flow rate of fluid received by the first sample probe may be equal to the flow rate of fluid received by the second sample probe. The test may be a stratification test. The component species may be at least one of O2, CO2, CO, SO2 and NOx. The sample of fluid received by at least one of the first and second sample probes may be received isokinetically. Determining the average concentration of the component species during the test may further include determining a third concentration of the component species of the fluid at a third location within the duct, and the first amount of time, the second amount of time and a third amount of time that fluid is received by a third sample probe at the third location is controlled based on the first, second and third concentrations of the component species determined during the test and the average concentration of the component species determined by the test. The first, second and third amounts of time that fluid is respectfully received by the first, second and third sample probes may be controlled so that a concentration of the component species collectively received by the first, second and third sample probes equals the average concentration of the component species determined during the test. The first, second and third concentrations of the component species determined during the test may be different from each other.

DETAILED DESCRIPTION

Figure 1:
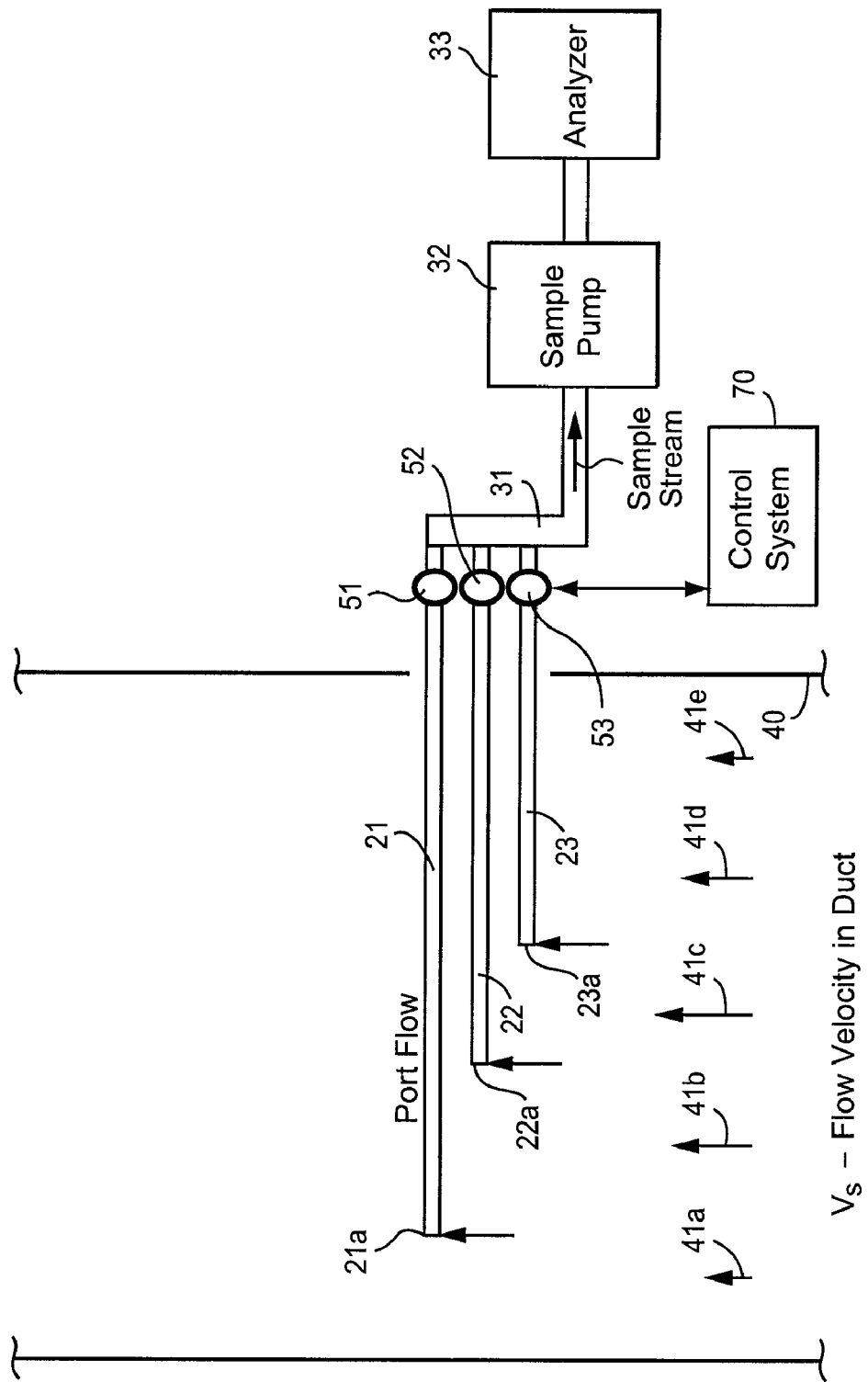
FIG. 1 is a diagram of a fluid sampling and continuous monitoring system for obtaining a spatially representative sample of fluid flowing through a duct in accordance with a first embodiment of the invention.

FIG. 1 illustrates an exemplary embodiment of a fluid sampling and monitoring system for obtaining a continuous and spatially representative sample of fluid flowing through duct 40. The fluid flowing through duct 40 may be, for example, exhaust gas containing pollutants from a gas turbine. Duct 40 may be, for example, an outlet exhaust stack of the gas turbine.

The sampling and monitoring system includes a plurality of sample probes 21–23, a plurality of flow controllers 51–53, sample pump 32 and sample analyzer 33. Sample probes 21–23 are spatially distributed within duct 40 and include inlet ports 21a–23a for receiving a sample of the fluid flowing through duct 40 at respective local positions. Sample passageway 31 fluidly connects flow controllers 51–53 and sample pump 32. Sample analyzer 33 is fluidly connected to sample pump 32.

A fluid flows through duct 40 at flow velocity Vs. However, the flow velocity of the fluid within different areas of duct 40 is often stratified. The flow velocity of the fluid thus has an uneven velocity profile such that local fluid velocities are unequal. This velocity profile is graphically illustrated by arrows 41a–41e where larger local flow velocities in duct 40 are illustrated by larger arrows. For example, the local flow velocity in the center of duct 40 is higher (as illustrated by arrow 41c) than the local flow velocities near the walls of duct 40 (as illustrated by arrows 41a and 41e).

The fluid flowing through duct 40 includes a component gas species such as NOx, CO2, CO, SO2 and/or O2. A time averaged concentration of one or more of these component gas species flowing through the entire duct 40 is determined. For example, an average concentration of a component gas species is determined by a point by point cross-duct stratification test of a relative accuracy test audit. The test may also include EPA manual testing methods.

As part of the test for determining the average concentration of the component gas species flowing through the entire duct 40, quantitative measurements of the component species" concentration are made at a plurality of locations within duct 40. The spatial coordinates of each of these locations is determined along with a time averaged local concentration level of the component gas species at those locations. The spatial coordinates of specific locations within duct 40 and its corresponding (time averaged) quantitative component gas species concentration level are thus identified during the test. The component gas species concentration levels of the identified locations may each have different quantitative levels.

After (i) the average concentration of the component gas species flowing through the entire duct 40 and (ii) the spatial coordinates of each of the locations and its corresponding local component species concentration levels are determined during the test, portions of the fluid flowing in duct 40 are received by sample probes 21–23 via inlet ports 21a–23a. Sample probes 21–23 are positioned within duct 40 so that each of sample probes 21–23 is capable of receiving fluid at the locations determined during the test. In particular, inlet ports 21a–23a are positioned at the spatial coordinates of respective locations determined during the test. The respective concentration levels of the component gas species received by inlet ports 21a–23a are therefore predetermined. That is, the concentration levels of the component gas species which can be received by inlet ports 21a–23a are equal to the concentration levels at the same spatial coordinates determined during the test.

Flow controllers 51–53 control the flow rate of fluid, and hence the flow rate of the amount of component gas species within the fluid, received by sample probes 21–23, respectively. Flow controllers 51–53 each may comprise a valve and a flow rate sensor. If any one the flow controller valves is closed, then no fluid is received by that sample probe 21–23 which is connected to that closed flow controller valve. The degree to which flow controller valves are opened controls the flow rate of fluid (and hence component gas species) received by a connected sample probe. A computerized control system 70 controls the degree of opening of each flow control valve. Alternatively, flow control valves can be opened and closed manually. Each of the flow control valves 51–53, when opened, communicates received fluid from sample probes 21–23, respectively, to sample stream passageway 31. Sample pump 32 draws the received fluid from passageway 31 to analyzer 33. Analyzer 33 performs an analysis on the received sample such as an identification of component gases.

In operation, the flow rates of fluid received by sample probes 21–23 are respectively controlled by flow controllers 51–53 based on the average concentration of the component gas species flowing through the entire duct 40 determined during the test and the local component gas species concentration levels at each of the locations determined during the test. In particular, the flow rates of fluid received by sample probes 21–23 are controlled by flow controllers 51–53 such that the collective sample received by analyzer 33 via sample stream passageway 31 and sample pump 32 has a component species concentration that is equal to the average concentration of the component gas species in duct 40 determined during the test.

As a specific example of operation, suppose it was determined during a test (e.g., a point by point cross-duct stratification test of a relative accuracy test audit) that the average concentration of NOx of the fluid in the entire duct 40 is 2 ppm and that the local average NOx concentration at a first spatial location within duct 40 is 1 ppm, the local average NOx concentration at a second spatial location within duct 40 is 2 ppm, and the local average NOx concentration at a third spatial location is 3 ppm. In this case, sample probe 21 is positioned so that inlet 21a receives fluid at the first spatial location. That is, inlet 21a will have the same spatial coordinates as the first spatial location having a NOx concentration of 1 ppm. Sample probe 22 is positioned so that inlet 22a receives fluid at the second spatial location. That is, inlet 22a will have the same spatial coordinates as the second spatial location having a NOx concentration of 2 ppm. Sample probe 23 is positioned so that inlet 23a receives fluid at the third spatial location. That is, inlet 23a will have the same spatial coordinates as the third spatial location having a NOx concentration of 3 ppm.

The flow controllers 51–53 will be set to respectively control the flow rates of fluid and hence NOx concentration concurrently received by sample probes 21–23 so that fluid collectively received by sample probes 21–23 will be equal to the average concentration (2 ppm) of NOx determined for the entire duct 40 during the test. In this example, each of the flow rates of sample probe 21 (receiving 1 ppm NOx), sample probe 22 (receiving 2 ppm NOx) and sample probe 23 (receiving 3 ppm NOx) will be equal to each other so that the NOx concentration of the collective sample received by sample probes 21–23 is equal to the average NOx concentration for the entire duct 40 determined during the test. The flow ratio between the flow rates of sample probes 21–23 as controlled by flow controllers 51–53 is 1:1:1 and thus equal amounts of fluid is received by each of the sample probes 21–23 in the foregoing example.

While the exemplary embodiment illustrated in FIG. 1 shows the use of three sample probes 21–23, it will be understood that any plurality of sample probes can be used. For example, sample probe 23 can be completely closed by flow controller 53 so that it does not receive any sample or be removed from duct 40 altogether.

As an example of operation of this system having two probes, suppose that a test was conducted indicating that the average concentration of O2 in the entire duct 40 was equal to 6 ppm and that in determining this average concentration, an (average) O2 concentration level at a first spatial location within duct 40 was measured as being 2 ppm and the (average) O2 concentration level at a second spatial location within duct 40 was measured as being 8 ppm. After the test is completed, sample probe 21 is positioned so that inlet 21a receives fluid at the first spatial location. That is, inlet 21a will have the same spatial coordinates as the first spatial location having an O2 concentration of 2 ppm. Sample probe 22 is positioned so that inlet 22a receives fluid at the second spatial location. That is, inlet 22a will have the same spatial coordinates as the second spatial location having an O2 concentration of 8 ppm.

Flow controllers 51–52 are set to respectively control the flow rates of fluid (and hence O2 concentration) concurrently received by sample probes 21–22 so that fluid collectively received by sample probes 21–22 will be equal to the average concentration (6 ppm) of O2 determined for the entire duct 40 during the test. Again, flow controller 53 completely closes sample probe 23 or is removed along with sample probe 23 altogether. In this example, the flow rates of sample probe 21 (receiving 2 ppm O2) and sample probe 22 (receiving 8 ppm O2) will be set in a 1:2 flow ratio so that the O2 concentration in the collective sample received by sample probes 21 and 22 is equal to the average O2 concentration (6 ppm) for the entire duct 40 determined during the test ((33.3% of total flow)(2 ppm)+(66.6% of total flow)(8 ppm)=6 ppm). The flow rates of sample probes 21 and 22 are set by flow controllers 51 and 52, respectively. The fluid received by sample probe 22 is twice the amount of fluid received by sample probe 21 in this example.

A representative sampling may thus be achieved which avoids selecting an over-estimated sampling location using a single point probe and complex multi-point sampling required for manual methods. After identifying two or more sample locations at different species concentrations, gas volume sampling at each location is controlled by setting the flow rate to dial in the component species of interest to closely approach or meet the average reading obtained during a test such as a stratification test of a relative accuracy test. Flow rate settings on flow controllers 51–53 may also be updated periodically.

In another exemplary embodiment of the present invention, flow controllers 51–53 in the system illustrated in FIG. 1 can be controlled so that length of time fluid is received (rather than flow rate as discussed above) from each of the locations determined during the test to provide a collective sample received by sample probes 21–23 that has a component gas species concentration which equals the average component gas species concentration level for the entire duct 40 determined during the test. In this exemplary embodiment, a test for determining the average component gas species concentration in duct 40 and the spatial locations within duct 40 with corresponding local gas species concentrations are first performed as discussed above. Assume, for example, that the average concentration of NOx of the fluid in the entire duct 40 is 2 ppm and that the local NOx concentration at a first spatial location within duct 40 is 1 ppm, the local NOx concentration at a second spatial location within duct 40 is 2 ppm, and the local NOx concentration at a third spatial location is 3 ppm. In this example, sample probe 21 is positioned so that inlet 21a receives fluid (having a local 1 ppm NOx concentration) at the first spatial location, sample probe 22 is positioned so that inlet 22a receives fluid (having a local 2 ppm NOx concentration) at the second spatial location, and sample probe 23 will positioned so that inlet 23a receives fluid (having a local 3 ppm NOx concentration) at the third spatial location.

The flow controllers 51–53 will be sequentially opened for a specific amount of time, either manually or via a computerized controller, to permit gas received to be collected for analysis. When one flow controller is opened, the other flow controllers will be closed. For example, as flow controller 51 is opened to allow sample probe 21 to receive the fluid having a local (average) 1 ppm NOx concentration, flow controllers 52 and 53 are closed so that no fluid is received by sample probes 22 and 23. Similarly, as flow controller 52 is opened to allow sample probe 22 to receive the fluid having a local (average) 2 ppm NOx concentration, flow controllers 51 and 53 are closed so that no fluid is received by sample probes 21 and 23. As flow controller 53 is opened to allow sample probe 23 to receive the fluid having a local (average) 3 ppm NOx concentration, flow controllers 51 and 52 are closed so that no fluid is received by sample probes 21 and 22. When opened, the flow rate received by each sample probe is equal to the respective flow rates of fluid received by the other sample probes when they are opened. That is, the pressure for drawing fluid provided by sample pump 32 remains constant so that fluid is received at the same rate irrespective of which flow controller is opened and the flow controller valves are opened to the same degree.

In the foregoing example, the amount of time that sample probe 21 (receiving 1 ppm NOx), sample probe 22 (receiving 2 ppm NOx) and sample probe 23 (receiving 3 ppm NOx) receive fluid are equal to each other so that the NOx concentration of the collective sample sequentially received by sample probes 21–23 is equal to the average NOx concentration for the entire duct 40 determined during the test. That is, the respective time amounts that flow controllers 51–53 are opened are equal to each other. When opened, each of the flow controllers 51–53 are opened to the same degree and the sample pump 32 draws fluid at the same rate. The ratio of time amounts that sample probes 21–23 are open is 1:1:1 and thus equal amounts of fluid are received by each of the sample probes 21–23 so that the collective sample has a NOx concentration of 2 ppm, the average NOx concentration determined during the test for the entire duct 40. The flow controllers 51–53 can be opened in any sequence, but when one flow controller is opened the other flow controllers are closed. For example, flow controller 52 can be opened for a certain amount of time (e.g., 1 minute) while flow controllers 51 and 53 are closed. Flow controller 51 is then opened for the same amount of time (1 minute) and the same degree of opening while flow controllers 52 and 53 are closed, and finally flow controller 53 is opened while flow controllers 51 and 52 are closed for the same amount of time (1 minute) and the same degree of opening.

Figure 2:
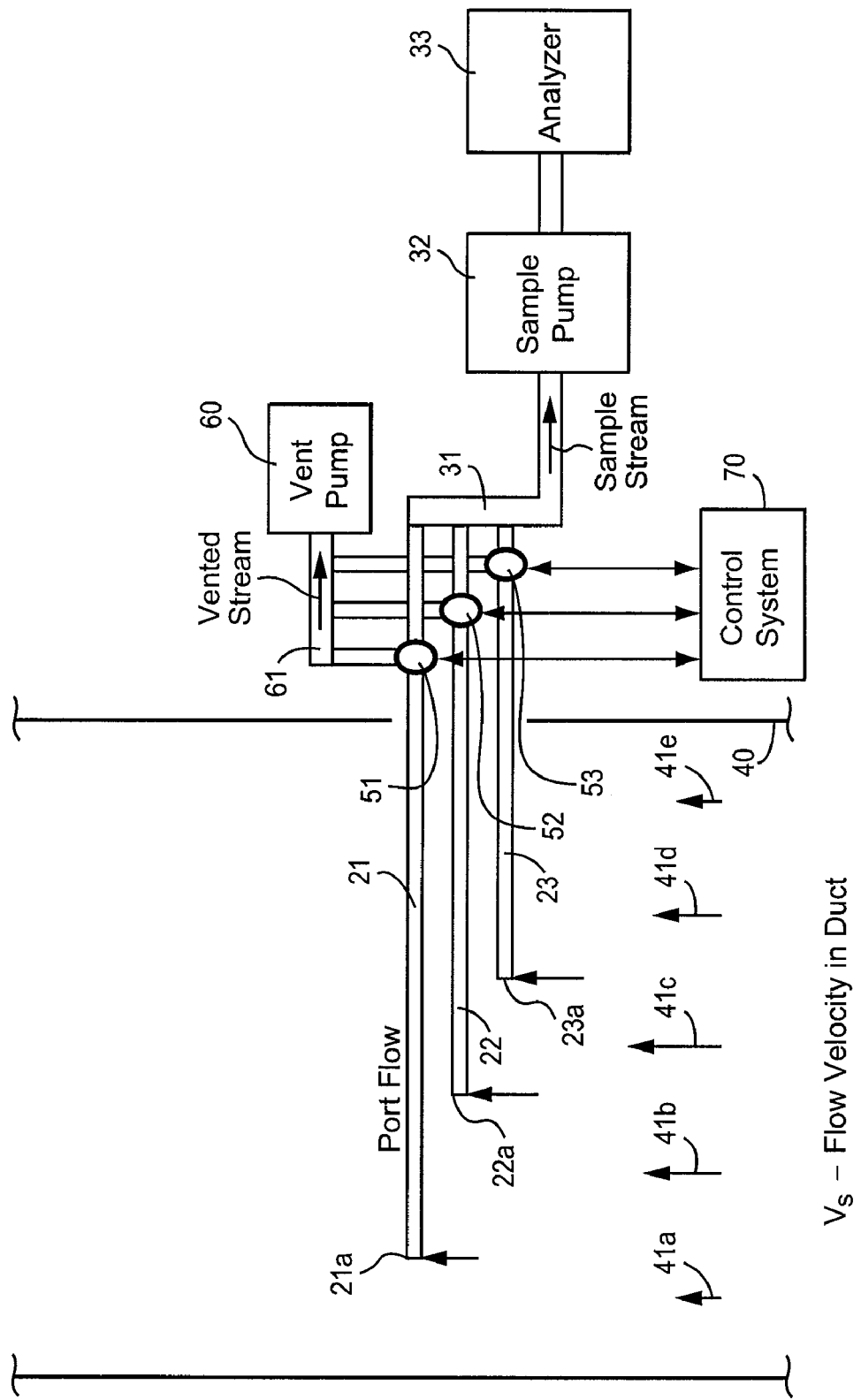
FIG. 2 is a diagram of a fluid sampling and continuous monitoring system for obtaining a spatially representative sample of fluid flowing through a duct in accordance with another embodiment of the invention.

FIG. 2 illustrates another exemplary embodiment of a fluid sampling and monitoring system for obtaining a spatially representative sample of a fluid, where identical reference numbers refer to parts common to previous embodiments. Only the differences from previous embodiments will be discussed in detail.

The system illustrated in FIG. 2 includes a vent pump 60. Vent pump 60 is capable of fluidly connecting to flow controllers 51–53 via vent passageway 61. Fluid entering sample probe 21–23 may be vented to the atmosphere via vent pump 60 and vent passageway 61. Flow controllers 21–23 may thus direct fluid entering probes 21–23 to venting passageway 61 so that the fluid is vented to the atmosphere or to sample passageway 31 so that the fluid is received for analysis. Vent pump 60 may optionally be removed so that fluid is vented directly to the atmosphere as long as atmospheric pressure is enough to draw fluid through venting passageway 61 and prevent back flow.

As discussed in a previous exemplary embodiment, flow controllers 51–53 can be controlled so that fluid is received from each of the locations determined during the test for a specific amount of time. In particular, the ratio of time amounts during which fluid is received by each sample probe 21–23 is defined so that the collective sample received by sample probes 21–23 has a component gas species concentration which equals the average component gas species concentration level for the entire duct 40 determined during the test. Flow controllers 51–53 are sequentially turned into a sampling position, either manually or via a computerized controller, to permit fluid including the component gas species to be received and collected for analysis via sample passageway 31. When one flow controller is in a sampling position to direct gas to sample passageway 31, the other flow controllers are in a venting position to direct any gas entering a connected sample probe to venting passageway 61. For example, as flow controller 51 is in a sampling position to allow sample probe 21 to receive the fluid at a first local position within duct 40, flow controllers 52 and 53 are in a venting position so that any fluid entering sample probes 22 and 23 is vented (e.g., to atmosphere) via venting passageway 61 and vent pump 60. Similarly, as flow controller 52 is in a sampling position to allow sample probe 22 to receive the fluid at a second local position within duct 40, flow controllers 51 and 53 are in a venting position so that any fluid entering sample probes 21 and 23 is vented via venting passageway 61 and vent pump 60. As flow controller 53 is in a sampling position to allow sample probe 23 to receive the fluid at another local position within duct 40, flow controllers 51 and 52 are in a venting position so that any fluid entering sample probes 21 and 22 is vented via venting passageway 61 and vent pump 60. By continuously venting the flow in the "standby" probes, gas is not held up in the sample probe where it can be converted. Any sequential order of turning flow controllers to direct fluid to sample stream passageway 31 can be used. However, an analysis provided by analyzer 33 is not initiated until all the necessary gas samples from sample probes 21–23 are obtained.

The amount of time that each of the flow controllers 51–53 is placed in the sampling position can be controlled so that cumulative fluid sequentially received by sample probes 21–23 has a component gas species concentration which is equal to the average component gas species concentration determined for the entire duct 40 during the test. When placed in the sampling position, the flow rate received by each sample probe 21–23 is equal to the respective other flow rates of fluid received by the other sample probes when they are in the sampling position. That is, the pressure for drawing fluid provided by sample pump 32 remains constant so that fluid is received at the same rate irrespective of which flow controller 51–53 is placed in the sampling position and the flow controllers 51–53 are opened to the same degree when placed in the sampling position.

The system illustrated in FIG. 2 thus includes two pumps: (i) sample pump 32 for sequentially (non-concurrently) pulling the sample flow from sampling probes 21–23 to analyzer 33 and (ii) vent pump 60 for continuously venting flow from the "standby" sample probes. This system is capable of performing isokinetic flow sampling such that the flow velocity received by inlet ports 21a–23a is equal to the local velocity of the fluid at the same spatial location within duct 40. Also, each sampling probe 21–23 may be equipped with a thermocouple and pitot tube pressure measurement device at each sample point to establish the sample flow velocity.

A multi-point representative sample can thus be obtained through the exemplary embodiments of the present invention utilizing flow rate control and/or time sequence control of flow controllers 51–53. Both flow rate control and time sequence control avoid holding up sample gas in sample probes 21–23 which could affect the actual species concentration. A single point sampling, which may be performed at a spatial point having an over-or underestimate of test gas species concentration can be avoided. Additionally, the actual emissions can be easily tuned to be representative of the manual multi-point method.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of obtaining a spatially representative sample of fluid flowing through a duct, the method comprising:
    determining an average concentration of a component species of the fluid flowing through the duct during a test which includes determining a first concentration of the component species at a first location within the duct and determining a second concentration of the component species at a second location within the duct;
    positioning a first sample probe in the duct so that the first sample probe receives a portion of the fluid at the first location;
    positioning a second sample probe in the duct so that the second sample probe receives a portion the fluid at the second location; and
    controlling respective flow rates of fluid received by the first and second sample probes based on the first concentration of the component species, the second concentration of the component species and the average concentration of the component species.

2. A method of claim 1 wherein the respective flow rates are controlled so that a concentration of the component species of the fluid collectively received by the first and second sample probes equals the average concentration of the component species determined during the test.

3. A method of claim 1 wherein the first and second concentrations of the component species determined during the test are different from each other.

4. A method of claim 1 wherein the fluid is received by the first and second sample probes concurrently.

5. A method of claim 1 wherein the flow rate of the fluid received by the first sample probe is controlled by a first flow controller connected to the first sample probe and the flow rate of the fluid received by the second sample probe is controlled by a second flow controller connected to the second sample probe.

6. A method of claim 1 wherein the test is a stratification test.

7. A method of claim 1 wherein the component species is at least one of O2, CO2, CO, SO2 and NOx.

8. A method of claim 1 wherein determining the average concentration of the component species during the test further includes determining at least a third concentration of the component species of the fluid at at least a third location within the duct, and further comprising positioning at least a third sample probe so that the third sample probe receives a portion of the fluid at the third location and controlling respective flow rates of fluid received by the first, second and third sample probes based on the first, second and third concentrations of the component species determined during the test and the average concentration of the component species determined by the test.

9. A method of claim 8 wherein the respective flow rates of fluid received by the first, second and third sample probes are controlled so that a concentration of the component species collectively received by the first, second and third sample probes equals the average concentration of the component species determined during the test.

10. A method of claim 8 wherein the first, second and third concentrations of the component species determined during the test are different from each other.

11. A method of obtaining a spatially representative sample of fluid flowing through a duct, the method comprising:
  determining an average concentration of a component species of the fluid flowing through the duct during a test which includes determining a first concentration of the component species at a first location within the duct and determining a second concentration of the component species at a second location within the duct;
  positioning a first sample probe in the duct so that the first sample probe receives a portion of the fluid at the first location;
  positioning a second sample probe in the duct so that the second sample probe receives a portion of the fluid at the second location; and
  controlling a first amount of time that the flow of fluid is received by the first sample probe and a second amount of time that the flow of fluid is received by the second sample probe based on the first concentration of the component species, the second concentration of the component species and the average concentration of the component species.

12. A method of claim 11 wherein the first amount of time and the second amount of time are controlled so that a concentration of the component species of the fluid collectively received by the first and second sample probes equals the average concentration of the component species determined during the test.

13. A method of claim 11 wherein the first and second concentrations of the component species determined during the test are different from each other.

14. A method of claim 11 wherein the fluid is received by the first and second sample probes non-concurrently.

15. A method of claim 14 further comprising venting fluid from the first sample probe when fluid is being received by the second sample probe.

16. A method of claim 15 further comprising venting fluid from the second sample probe when the fluid is being received by the first sample probe.

17. A method of claim 11 wherein the first amount of time that the fluid is received by the first sample probe is controlled by a first flow controller connected to the first sample probe and the second amount of time that the fluid received by the second sample probe is controlled by a second flow controller connected to the second sample probe.

18. A method of claim 17 wherein at least one of the first and second flow controllers is coupled to both a sample pump and a venting pump.

19. A method of claim 17 wherein the first flow controller vents fluid from the first sample probe when the second flow controller communicates fluid received by the second flow controller to a sample pump.

20. A method of claim 19 wherein the second flow controller vents fluid from the second sample probe when the first flow controller communicates fluid received by the first flow controller to a sample pump.

21. A method of claim 11 wherein the flow rate of fluid received by the first sample probe is equal to the flow rate of fluid received by the second sample probe.

22. A method of claim 11 wherein the test is a stratification test.

23. A method of claim 11 wherein the component species is at least one of O2, CO2, CO, SO2 and NOx.

24. A method of claim 11 wherein the fluid received by at least one of the first and second sample probes is received isokinetically.

25. A method of claim 11 wherein determining the average concentration of the component species during the test further includes determining at least a third concentration of the component species of the fluid at at least a third location within the duct, and the first amount of time, the second amount of time and at least a third amount of time that fluid is received by at least a third sample probe at the third location is controlled based on the first, second and third concentrations of the component species determined during the test and the average concentration of the component species determined by the test.

26. A method of claim 25 wherein the first, second and third amounts of time that fluid is respectfully received by the first, second and third sample probes are controlled so that a concentration of the component species collectively received by the first, second and third sample probes equals the average concentration of the component species determined during the test.

27. A method of claim 25 wherein the first, second and third concentrations of the component species determined during the test are different from each other.

28. A system for obtaining a spatially representative sample of fluid flowing through a duct in which an average concentration of a component species of the fluid flowing through the duct has been determined during a test which includes determining a first concentration of the component species at a first location within the duct and determining a second concentration of the component species at a second location within the duct, the system comprising:
  a first sample probe positioned in the duct so that the first sample probe receives a portion of the fluid at the first location; and
  a second sample probe positioned in the duct so that the second sample probe receives a portion the fluid at the second location;
  wherein respective flow rates of fluid received by the first and second sample probes are controlled based on the first concentration of the component species, the second concentration of the component species and the average concentration of the component species.

29. A system of claim 28 wherein the respective flow rates are controlled so that a concentration of the component species of the fluid collectively received by the first and second sample probes equals the average concentration of the component species determined during the test.

30. A system of claim 28 wherein the first and second concentrations of the component species determined during the test are different from each other.

31. A system of claim 28 wherein the fluid is received by the first and second sample probes concurrently.

32. A system of claim 28 wherein the flow rate of the fluid received by the first sample probe is controlled by a first flow controller connected to the first sample probe and the flow rate of the fluid received by the second sample probe is controlled by a second flow controller connected to the second sample probe.

33. A system of claim 32 wherein the first and second flow controllers are operatively connected to a computerized control system.

34. A system of claim 28 wherein determining the average concentration of the component species during the test further includes determining at least a third concentration of the component species of the fluid at at least a third location within the duct, and the system further comprises at least a third sample probe positioned so that the third sample probe receives a portion of the fluid at the third location and controlling respective flow rates of fluid received by the first, second and third sample probes based on the first, second and third concentrations of the component species determined during the test and the average concentration of the component species determined by the test.

35. A system of claim 34 wherein the respective flow rates of fluid received by the first, second and third sample probes are controlled so that a concentration of the component species collectively received by the first, second and third sample probes equals the average concentration of the component species determined during the test.

36. A system of claim 34 wherein the first, second and third concentrations of the component species determined during the test are different from each other.

37. A system for obtaining a spatially representative sample of fluid flowing through a duct in which an average concentration of a component species of the fluid flowing through the duct has been determined during a test which includes determining a first concentration of the component species at a first location within the duct and determining a second concentration of the component species at a second location within the duct, the system comprising:

a first sample probe positioned in the duct so that the first sample probe receives a portion of the fluid at the first location; and a second sample probe positioned in the duct so that the second sample probe receives a portion of the fluid at the second location;

wherein a first amount of time that the flow of fluid is received by the first sample probe and a second amount of time that the flow of fluid is received by the second sample probe are controlled based on the first concentration of the component species, the second concentration of the component species and the average concentration of the component species.

38. A system of claim 37 wherein the first amount of time and the second amount of time are controlled so that a concentration of the component species of the fluid collectively received by the first and second sample probes equals the average concentration of the component species determined during the test.

39. A system of claim 37 wherein the first and second concentrations of the component species determined during the test are different from each other.

40. A system of claim 37 wherein the fluid is received by the first and second sample probes non-concurrently.

41. A system of claim 40 wherein fluid is vented from the first sample probe when fluid is being received by the second sample probe.

42. A system of claim 41 wherein fluid is vented from the second sample probe when the fluid is being received by the first sample probe.

43. A system of claim 37 wherein the first amount of time that the fluid is received by the first sample probe is controlled by a first flow controller connected to the first sample probe and the second amount of time that the fluid received by the second sample probe is controlled by a second flow controller connected to the second sample probe.

44. A system of claim 43 wherein the first and second flow controllers are operatively connected to a computerized control system.

45. A system of claim 43 wherein at least one of the first and second flow controllers is coupled to both a sample pump and a venting pump.

46. A system of claim 43 wherein the first flow controller vents fluid from the first sample probe when the second flow controller communicates fluid received by the second flow controller to a sample pump.

47. A system of claim 46 wherein the second flow controller vents fluid from the second sample probe when the first flow controller communicates fluid received by the first flow controller to a sample pump.

48. A system of claim 37 wherein the flow rate of fluid received by the first sample probe is equal to the flow rate of fluid received by the second sample probe.

49. A system of claim 37 wherein the fluid received by at least one of the first and second sample probes is received isokinetically.

50. A system of claim 37 wherein determining the average concentration of the component species during the test further includes determining at least a third concentration of the component species of the fluid at at least a third location within the duct, and the first amount of time, the second amount of time and at least a third amount of time that fluid is received by at least a third sample probe at the third location is controlled based on the first, second and third concentrations of the component species determined during the test and the average concentration of the component species determined by the test.

51. A system of claim 50 wherein the first, second and third amounts of time that fluid is respectfully received by the first, second and third sample probes are controlled so that a concentration of the component species collectively received by the first, second and third sample probes equals the average concentration of the component species determined during the test.

52. A system of claim 51 wherein the first, second and third concentrations of the component species determined during the test are different from each other.

53. A system for obtaining a spatially representative sample of fluid flowing through a duct in which an average concentration of a component species of the fluid flowing through the duct during a test which includes determining a first concentration of the component species at a first location within the duct and determining a second concentration of the component species at a second location within the duct, the system comprising:

a first means for sampling positioned in the duct so that the first means for sampling receives a portion of the fluid at the first location;

at least a second means for sampling positioned in the duct so that the second means for sampling receives a portion the fluid at the second location; and means for controlling respective flow rates of fluid received by the first and second means for sampling based on the first concentration of the component species, the second concentration of the component species and the average concentration of the component species.

54. A system of claim 53 wherein the respective flow rates are controlled by the means for controlling so that a concentration of the component species of the fluid collectively received by the first and second means for sampling equals the average concentration of the component species determined during the test.

55. A system of claim 53 wherein the first and second concentrations of the component species determined during the test are different from each other.

56. A system of claim 53 wherein the fluid is received by the first and second means for sampling concurrently.

57. A system for obtaining a spatially representative sample of fluid flowing through a duct in which an average concentration of a component species of the fluid flowing through the duct during a test which includes determining a first concentration of the component species at a first location within the duct and determining a second concentration of the component species at a second location within the duct, the system comprising:
- a first means for sampling positioned in the duct so that the first means for sampling receives a portion of the fluid at the first location;
- at least a second means for sampling positioned in the duct so that the second means for sampling receives a portion of the fluid at the second location; and
- means for controlling a first amount of time that the flow of fluid is received by the first means for sampling and a second amount of time that the flow of fluid is received by the second means for sampling based on the first concentration of the component species, the second concentration of the component species and the average concentration of the component species.

58. A system of claim 57 wherein the first amount of time and the second amount of time are controlled by the means for controlling so that a concentration of the component species of the fluid collectively received by the first and second means for sampling equals the average concentration of the component species determined during the test.

59. A system of claim 57 wherein the first and second concentrations of the component species determined during the test are different from each other.

60. A system of claim 57 wherein the fluid is received by the first and second means for sampling non-concurrently.

61. A system of claim 60 wherein fluid from the first means for sampling is vented when fluid is being received by the second means for sampling.

62. A system of claim 61 wherein fluid from the second means for sampling is vented when the fluid is being received by the first means for sampling.

63. A system of claim 57 wherein the flow rate of fluid received by the first means for sampling is equal to the flow rate of fluid received by the second means for sampling.

* * * * *